US00PP09496P

United States Patent [19]

Endisch et al.

[11] Patent Number: Plant 9,496

[45] Date of Patent: Apr. 2, 1996

[54] GERANIUM PLANT NAMED 'MORELLA'

[75] Inventors: Gerd Endisch, Geranienweg, D-76767 Hagenbach; Ursula Endisch-Burmeister, Bad Kreuznach, both of Germany; Wolf Endisch, Valle Guerra/Teneriffa, Spain

[73] Assignee: Gerd Endisch, Hagenbach, Germany

[21] Appl. No.: 384,009

[22] Filed: Feb. 6, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Willian Brinks Hofer Gilson & Lione

[57] ABSTRACT

A new and distinct cultivar of geranium known by the cultivar name 'Morella' is characterized by a crimson red flower color, dark foliage without strong zonation, a semi-double flower form, early flower response and a medium habit.

1 Drawing Sheet

BACKGROUND OF THE NEW PLANT

The present invention comprises a new and distinct cultivar of geranium botanically known as *Pelargonium zonale*, and hereinafter referred to by the cultivar name 'Morella'.

'Morella' is a product of planned breeding program which had the objective of creating new geranium cultivars with crimson/red-cherry/red flower color, dark foliage, medium habit.

'Morella' was originated from a hybridization made in a controlled breeding program in Hagenbach, Germany in 1990. The female parent was 'Cherry', characterized by its crimsom to ruby red flower color, large umbels, its tolerance to high light, and sensitive foliage. The male parent of 'Morella' was 'Osna', characterized by its signal-red, single flower form, dark foliage, late flower response and weak branching pattern.

'Morella' was discovered and selected as one flowering plant within the progency of the stated cross by the inventors in August 1991 in a controlled environment in Hagenbach, Germany.

DESCRIPTION OF THE NEW PLANT

The first act of asexual reproduction of 'Morella' was accomplished when vegetative cuttings were taken from the initial selection in January 1992 in a controlled environment in Hagenbruch, Germany, by a technician working under formulations established and supervised by Gerd Endisch.

Horticultural examination of selected units initiated in May 1992 has demonstrated that the combination of characteristics as herein disclosed for 'Morella' are firmly fixed and are retained through successive generations of asexual reproduction.

'Morella' has not been observed under all possible environmental conditions. The phenotype may vary significantly with variations in environment such as temperature, light intensity, and day length. The following observations, measurements, and comparisons describe plants grown in Hagenbach, Germany, under field conditions which approximate those generally used in commercial practice. The measurements and dimensions below are approximate.

The following traits have been repeatedly observed and are determined to be basic characteristics of 'Morella' to distinguish this geranium as a new and distinct cultivar:

1. crimson red flower color 2. dark foliage without strong zonation
3. semi-double flower form
4. early flower response
5. medium habit Of the many commercial cultivars known to the present inventor, the most similar in comparison to 'Morella' is 'Atlantis'. Reference is made to Chart A below which compares certain characteristics of Atlantis to those same characteristics of Atlantis. In comparison to 'Atlantis', 'Morella' has a more vigorous growth, better heat and light resistance, larger umbels and less flowers.

BRIEF DESCRIPTION OF THE DRAWING

The accompanying photographic drawing show typical flower and foliage characteristics of 'Morella', with colors being as true as possible with illustrations of this type.

DETAILED BOTANICAL DESCRIPTION

In the following description color references are made to The Royal Horticultural Society Colour Chart (R.H.S.). The color values are determined indoors from plants grown outdoors in August 1994 in Hagenbach, Germany, or Hannover (Bundessortenamt).

Classification:

*Botanical.*—A hybrid of the species *Pelargonium zonale*

*Commercial.*—Zonal geranium, cv. 'Morella'.

Inflorescence:

*Umbel.*—Comprises approx. 38 flowers.

*Average diameter.*—Approx. 100 mm.

*Average depth.*—Approx. 46–48 mm.

*Peduncle length.*—Approx. 140 mm.

*Spring flowering response period.*—In Hannover 1993: first flower early to mid April.

*Outdoor flower production.*—The flower count in 1993 indicated between 60–65 flowers per plant for May 15 through August 15 observation period.

*Durability.*—Medium rain resistance.

Corolla:

*Blooming habit.*—Continuous; until frost destroys plant.

*Average diameter.*—Approx. 43–45 mm.

*Form.*—Semi-double; cup-shaped when bloom first opens; flattening to shallow cup with maturity.

*Color.*—(General tonality from a distance of three meters) crimson red.

*Petals.*—Normally 8.

*Color of upper petals.*—R.H.S. 53 D.

*Color of lower petals.*—R.H.S. 56 C.

*Petaloids.*—Normally 1–3.

*Color (petaloids).*—R.H.S. 53 D.

*Pedicel length.*—Approx. 30 mm.

*Pedicel color.*—Red (anthocyanin colored).

*Persistence.*—Non-shattering flower.

Bud:

*Shape.*—Initially ovate.

*Size.*—Approx. 1.5–2.0 cm across.

*Color.*—Green with anthocyanin at the base.

*Sepals.*—Normally 5; pointed linear lanceolate; at time of petal appearance, approx. 10 mm in length.

Reproductive organs:

*Stamens: Anthers:* 5–8. Filaments: Approx. 5–7 mm in length. Pollen: Orange.

*Pistil.*—No.: 1. Length: Approx. 9 mm. Stigma: 5 lobes; red colored. Style: Approx. 3 mm in length; red colored.

*Ovaries.*—Green.

*Fruit.*—Partially fertile.

Plant:

*Foliage.*— Size: Approx. 9–10 cm across. Shape: Kidney-shaped. Texture: Leathery. Ribs and veins: Palmate venation. Margin: Bicrenate. Color (upper surface): Dark green, R.H.S. 137 A/B. Color (zonation): Green (weak).

*General appearance and form.*—Bushy. Internode length: Approx. 22 mm. Branching pattern: self-branching from base; very good branching characteristic; 25 branches observed 15 Aug., 1994. Height: Approx. 19–21 cm from media surface. Strength: Good shipping ability as rooted or unrooted cuttings.

*Petioles.*—Approx. 7–8 cm in length; green.

Chart A

| | New Cultivar Name: 'Morella' | Comparison Cultivar Name: 'Atlantis' |
|---|---|---|
| Flower count | 60–65<br>15 Aug. 94 | 65–70 |
| Habit | more vigorous | less vigorous |
| Heat resistance | good | bad |
| Umbel | larger: 100 mm | 95-mm |

What is claimed is:

1. A new and distinct cultivar of geranium plant known as 'Morella', as described and illustrated and particularly characterized by a crimson red flower color, dark foliage without strong zonation, a semi-double flower form, early flower response and a medium habit.

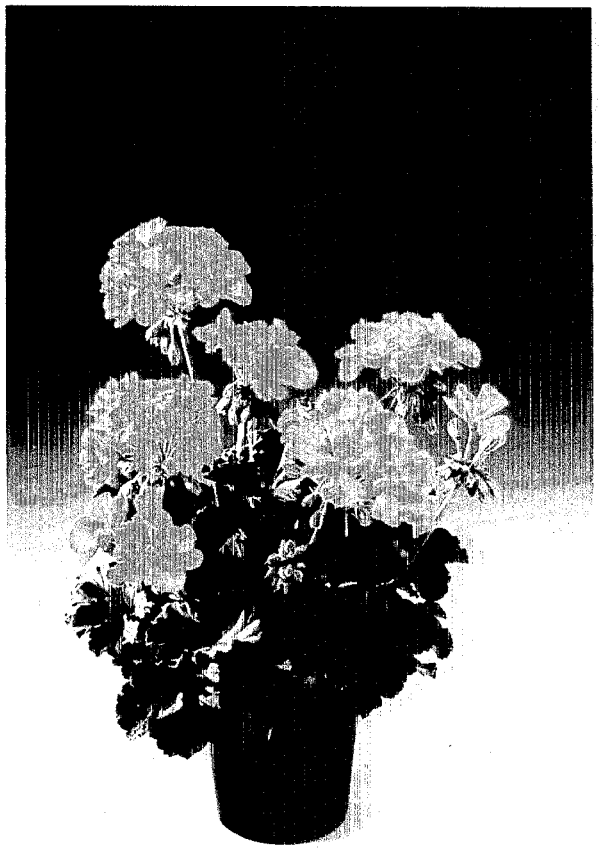

* * * * *